United States Patent
Ludwig

(10) Patent No.: US 8,012,508 B2
(45) Date of Patent: Sep. 6, 2011

(54) METHOD OF TARGETING SUSTAINED RELEASE FORMULATIONS OF THERAPEUTIC AGENTS TO TREAT LUNG DISEASES

(75) Inventor: Florian N. Ludwig, Mountain View, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 769 days.

(21) Appl. No.: 12/014,710

(22) Filed: Jan. 15, 2008

(65) Prior Publication Data

US 2009/0181096 A1    Jul. 16, 2009

(51) Int. Cl.
*A61K 9/14* (2006.01)
*A61P 11/00* (2006.01)

(52) U.S. Cl. ........ 424/489; 424/500; 424/501; 514/826; 514/888; 514/924; 514/951

(58) Field of Classification Search ........................ None
See application file for complete search history.

(56) References Cited

U.S. PATENT DOCUMENTS

| 6,077,256 | A | * | 6/2000 | Mann | 604/500 |
| 2004/0076586 | A1 | * | 4/2004 | Koening et al. | 424/46 |
| 2007/0274907 | A1 | * | 11/2007 | Li et al. | 424/1.11 |

FOREIGN PATENT DOCUMENTS

WO    WO 2005102280 A1 * 11/2005

* cited by examiner

*Primary Examiner* — Ernst V Arnold
*Assistant Examiner* — Christopher R Lea
(74) *Attorney, Agent, or Firm* — Squire, Sanders & Dempsey (US) LLP

(57) ABSTRACT

The present invention relates to method of targeting therapeutic agents for treating lung diseases.

8 Claims, No Drawings

METHOD OF TARGETING SUSTAINED RELEASE FORMULATIONS OF THERAPEUTIC AGENTS TO TREAT LUNG DISEASES

FIELD OF THE INVENTION

This invention relates to the fields of organic chemistry, pharmaceutical chemistry, polymer science, material science and medicine. In particular, it relates to a methods of targeting sustained release formulations of therapeutic agents to treat lung diseases.

BACKGROUND OF THE INVENTION

Chronic obstructive pulmonary disease (COPD) is a term that encompasses a group of chronic lung conditions characterized by obstruction of the airways of the lungs. COPD generally includes two major breathing diseases: chronic (obstructive) bronchitis and emphysema. Both breathing diseases make breathing difficult and cause breathlessness. COPD may be, but not necessarily, accompanied by primary pulmonary hypertension (PPH) or secondary pulmonary hypertension (SPH).

Chronic bronchitis is an progressive inflammatory disease that begins in the smaller airways within the lungs and gradually advances to larger airways. It increases mucous production in the airways and increases the occurrence of bacterial infection in the bronchial tree, which, in turn, impedes airflow. This chronic inflammation induces thickening of the walls of the bronchial tree leading to increased congestion in the lungs, which results in dyspnea. By definition, chronic bronchitis, refers to a productive cough for at least three months of each of two successive years for which other causes have been ruled out.

Emphysema comprises COPD that damages and destroys lung architecture with enlargement of the airspaces and loss of alveolar surface area. Lung damage is caused by weakening and breaking of air sacks, i.e., alveoli, within the lungs. Several adjacent alveoli may rupture, forming one large space instead of many small ones. Larger spaces can combine into an even bigger cavity, called a bulla. As a result, natural elasticity of the lung tissue is lost, leading to overstretching and rupture. There also is less pull on the smaller bronchial tubes, which can cause them to collapse and thus obstruct airflow. Air that is not exhaled before new air is inhaled gets trapped in the lungs, leading to shortness of breath. The sheer effort it takes a person suffering from emphysema to force air out of the lungs when exhaling can be exhausting.

COPD is always accompanied by bronchial obstruction. Thus, the most common symptoms of COPD include, shortness of breath, chronic coughing, chest tightness, greater effort to breathe, increased mucous production and frequent clearing of the throat. Patients are often unable to perform their daily activities. Independent development of chronic bronchitis and emphysema is possible, but most people with COPD have a combination of the two disorders. Both conditions decrease the ability of the lungs to take in oxygen and remove carbon dioxide.

Tuberculosis is another important lung disease. Tuberculosis most commonly attacks the lungs, but can also affect the central nervous system, the lymphatic system, the circulatory system, the genitourinary system, bones, joints and even the skin. Several Mycobacteria such as *Mycobacterium tuberculosis, Mycobacterium bovis, Mycobacterium africanum, Mycobacterium canetti*, and *Mycobacterium microti* can also cause tuberculosis. Symptoms of tuberculosis include a severe cough that lasts, weight loss, coughing up blood or mucus, weakness or fatigue, fever and chills, night sweats, loss of appetite.

Lung cancer is a particularly deadly lung disease. Typically, treatment of lung cancer includes systematic administration of chemotherapeutic agents, e.g., cytotoxic agents, to patients. Often such administration is associated with adverse side effects including nephrotoxicity and bone marrow toxicity. The nephrotoxicity limits the frequency at which clinicians can administer antitumor agents to patients. The prolonged time periods for systematic administration of antitumor agents leads to increased patient discomfort and inconvenience which may lead to decreased patient compliance.

Inhalation therapies may be attractive alternatives to some lung diseases because of reduced cost. However, current inhalation therapies have significant disadvantages which have limited their use in this area such as: no enhanced targeting to diseased cells, no protection from in vivo degradation in the lungs and short term therapeutic effects due to rapid clearance of the drug from the lung, requiring frequent administration of the drug.

What is needed is a method of targeting sustained release formulations of therapeutic agents for treating lung diseases. The current invention provides such methods.

SUMMARY OF THE INVENTION

Thus, in one aspect, the current invention relates to a method for treating lung disease, comprising:
  providing a plurality of particles that have a smallest cross-sectional dimension of about 10 microns;
  encapsulating within, adhering to, or incorporating into the structure of, the particles a therapeutic agent; and
  administering the particles directly into the right ventricle or right atrium of the heart or into that the venous system feeding the right atrium of the heart or the pulmonary artery.

In an aspect of this invention, the plurality of particles are selected from the group consisting of hydrogel particles, polymer particles and porous silica particles.

In an aspect of this invention, the method of administering the particles comprises intravenous delivery.

In an aspect of this invention, the method of administering the particles comprises direct injection into the right ventricle or right atrium of the heart.

In an aspect of this invention, the method of administering the particles comprises using a catheter.

In an aspect of this invention, the particles are biodegradable.

In an aspect of this invention, the therapeutic agent elutes from the particle over a period from about 1 hour to about 1 year.

In an aspect of this invention, the therapeutic agent elutes from the particle over a period from about 1 day to about 1 month.

In an aspect of this invention, the lung disease is selected from the group consisting of asthma, chronic obstructive pulmonary disease (COPD), chronic bronchitis, emphysema, pulmonary hypertension, pulmonary fibrosis, sarcoidosis, influenza, pneumonia, tuberculosis and lung cancer.

DETAILED DESCRIPTION OF THE INVENTION

Use of the singular herein includes the plural and visa versa unless expressly stated to be otherwise. That is, "a" and "the" refer to one or more of the word or phrase that follows. For example, "a therapeutic agent" includes one such agent, two such agents, etc. Likewise, "the layer" may refer to one, two or more layers and "the polymer" may mean one polymer or a plurality of polymers. By the same token, words such as, without limitation, "layers" and "polymers" would refer to one layer or polymer as well as to a plurality of layers or polymers unless, again, it is expressly stated or obvious from the context that such is not intended.

As used herein, "therapeutic agent" refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

As used herein, the terms "drug" and "therapeutic agent" are used interchangeably.

As used herein, "treating" refers to the administration of a therapeutically effective amount of a therapeutic agent to a patient known or suspected to be suffering from a lung disease.

A "therapeutically effective amount" refers to that amount of a therapeutic agent that will have a beneficial affect, which may be preventative, curative or palliative, on the health and well-being of the patient with regard to the lung disease with which the patient is known or suspected to be afflicted. A therapeutically effective amount may be administered as a single bolus, as intermittent bolus charges, as short, medium or long term sustained release formulations or as any combination of these. As used herein, short-term sustained release refers to the administration of a therapeutically effective amount of a therapeutic agent over a period from about several hours to about 3 days. Medium-term sustained release refers to administration of a therapeutically effective amount of a therapeutic agent over a period from about 3 day to about 14 days and long-term refers to the delivery of a therapeutically effective amount over any period in excess of about 14 days.

As used herein, "lung disease" includes, without limitation, asthma, chronic obstructive pulmonary disease (COPD), chronic bronchitis, emphysema, pulmonary hypertension, pulmonary fibrosis, sarcoidosis, influenza, pneumonia, tuberculosis and lung cancer.

As used herein, "asthma" refers to a chronic illness involving the respiratory system in which the airway occasionally constricts, becomes inflamed, and is lined with excessive amounts of mucus, often in response to one or more triggers such as exposure to an environmental stimulant (or allergen) such as cold air, warm air, moist air, exercise or exertion, or emotional stress. In children, the most common triggers are viral illnesses such as those that cause the common cold. This airway narrowing causes symptoms such as wheezing, shortness of breath, chest tightness, and coughing. In asthma, reversible airway obstruction is caused by inflammation, contraction of the airway smooth muscle, increased mucus secretion, and plugging of the bronchioles.

As used herein, "chronic obstructive pulmonary disease (COPD)" refers to a group of diseases characterized by a pathological limitation of airflow in the airway that is not fully reversible. That is, COPD is the umbrella term for chronic bronchitis, emphysema and a range of other lung disorders. Cigarette smoking is the most common cause of COPD but it can be caused to other airborne irritants such as coal dust, asbestos or solvents, and congenital conditions such as alpha-1-antitrypsin deficiency. Breathing in other kinds of lung irritants, like pollution, dust, or chemicals, over a long period of time may also contribute to COPD. The airways branch out like an upside-down tree, and at the end of each branch are many small, balloon-like air sacs called alveoli. In healthy people, each airway is clear and open. The air sacs are small and dainty, and both the airways and air sacs are elastic and springy. In COPD, the airways and air sacs lose their shape and become floppy. As a result, less air gets into the lungs and less air is expelled from the lungs because: the airways and air sacs lose their elasticity (like an old rubber band), the walls between many of the air sacs are destroyed, the walls of the airways become thick and inflamed and cells in the airways make more mucus than usual, which tends to clog the airways.

As used herein, "chronic bronchitis" refers to a chronic obstructive pulmonary disease (COPD) in which airway obstruction results from chronic and excessive secretion of abnormal airway mucus, inflammation, bronchospasm, and infections. Chronic bronchitis is characterized by hypersecretion of mucus accompanied by a chronic productive cough. Tobacco and infectious agents are major causes of chronic bronchitis.

As used herein, "emphysema" refers to a chronic obstructive pulmonary disease (COPD) in which a structural element (elastin) in the terminal bronchioles is destroyed leading to collapse of the airway walls and resultant inability to exhale "stale" air. Emphysema is caused by loss of elasticity of the lung tissue due to destruction of structures supporting the alveoli, and destruction of capillaries feeding the alveoli. The result is that small airways collapse during exhalation, leading to intrapment of air in the lungs. Symptoms include shortness of breath on exertion (typically when climbing stairs or inclines, and later at rest), hyperventilation, and an expanded chest.

As used herein, "pulmonary hypertension" refers to a disorder in which the blood pressure in the pulmonary arteries is abnormally high. In severe pulmonary hypertension, the right side of the heart must work harder than usual to pump blood against the high pressure. When this continues for long periods, the right heart enlarges and functions poorly, and fluid collects in the ankles (edema) and the belly. Eventually the left side of the heart begins to fail. Heart failure caused by pulmonary disease is called cor pulmonale. When pulmonary hypertension occurs in the absence of any other disease, it is called primary pulmonary hypertension.

As used herein, "pulmonary fibrosis" refers to a disease of the lungs characterized by an abnormal and excessive deposition of fibrous connective tissue in the pulmonary interstitium with minimal associated inflammation.

As used herein, "sarcoidosis" refers to a disease of the lungs which involves inflammation that produces tiny lumps of cells in lungs or other organs. The lumps are called granulomas. They are very small and can be seen only with a microscope. These tiny granulomas can grow and clump together, making many large and small groups of lumps. If many granulomas form in an organ, they can affect how the organ works. This can cause symptoms of sarcoidosis. Sarcoidosis can occur in almost any part of your body, although it usually affects some organs more than others. It usually starts in one of two places: lungs and lymph nodes. Sarcoidosis often affects skin, eyes, liver. Sarcoidosis almost always occurs in more than one organ at a time. Sarcoidosis has an active and a nonactive phase. In the active phase, the granulomas form and grow. In this phase, symptoms can develop, and scar tissue can form in the organs where the granulomas occur. In the nonactive phase, the inflammation goes down, and the granulomas stay the same size or shrink. But the scars may remain and cause symptoms. Changes in sarcoidosis usually occur slowly (e.g., over months). Sarcoidosis does not usually cause sudden illness. However, some symptoms may occur suddenly. They include: disturbed heart rhythms, arthritis in the ankles, eye symptoms.

As used herein, "influenza" refers to a contagious respiratory illness or infection caused by a number of viruses. Symptoms of the flu include extreme tiredness, muscle aches, chills, cough, fever, headache, sore throat, runny or stuffy nose, nausea, vomiting, and diarrhea. Influenza viruses are divided into three types, designated A, B, and C. Influenza types A and B are responsible for epidemics of respiratory illness that occur almost every winter and are often associated with increased rates of hospitalization and death. Type C infection usually causes either a very mild respiratory illness or no symptoms at all; it does not cause epidemics and does not have the severe public health impact of influenza types A and B.

As used herein, "pneumonia" refers to an inflammatory infection that can be caused by different types of microorganisms, including bacteria, viruses, and fungi. Some common symptoms associated with pneumonia include fever, chills, cough, difficulty in breathing, unusually rapid breathing, breathing with grunting or wheezing sounds, labored breathing that makes a child's rib muscles retract when muscles under the rib cage or between ribs draw inward with each breath, vomiting, chest pain, abdominal pain, decreased activity, loss of appetite or poor feeding (in infants) and in extreme cases, bluish or gray color of the lips and fingernails. The most common cause of bacterial pneumonia is *Streptococcus pneumoniae*. In this form of pneumonia, there is usually an abrupt onset of the illness with shaking chills, fever, and production of a rust-colored sputum. The infection spreads into the blood in 20-30% of cases, and if this occurs, 20-30% of these patients die. *Hemophilus influenza* is a bacterium that often causes pneumonia in people suffering from chronic obstructive pulmonary disease (COPD) or alcoholism. *Mycoplasma pneumonia* is a slowly developing infection. Symptoms include fever, chills, muscle aches, diarrhea, and rash. This bacterium is the principal cause of many pneumonias in the summer and fall months and is often referred to as "atypical pneumonia." Some viruses that cause pneumonia are adenoviruses, rhinovirus, influenza virus (flu), respiratory syncytial virus (RSV), and parainfluenza virus. Viral pneumonias do not typically respond to antibiotic treatment. These pneumonias usually resolve over time with the body's immune system fighting off the infection. It is important to make sure that a bacterial pneumonia does not secondarily develop. If it does, then the bacterial pneumonia is treated with appropriate antibiotics. Fungal infections that can lead to pneumonia include actinomycosis, nocardiosis, histoplasmosis, coccidiomycosis, blastomycosis, aspergillosis, and cryptococcosis. The inflammatory response of lungs in a patient suffering from pneumonia varies depending on the type of infection, and might include: lobar consolidation: solidification of the lung as air spaces are filled with fluid and cellular material, and interstitial inflammation. Pneumonia is sometimes accompanied by necrosis (tissue changes accompanying cell death), cavitation (hollow spaces walled off by scar tissue), abscesses (pus formation), and granuloma formation (tumor-like masses of different kinds of cells).

As used herein, "tuberculosis" refers to a infectious disease caused mainly by *Mycobacterium tuberculosis*. Tuberculosis most commonly attacks the lungs, but can also affect the central nervous system, the lymphatic system, the circulatory system, the genitourinary system, bones, joints and even the skin. Other Mycobacteria such as *Mycobacterium bovis, Mycobacterium africanum, Mycobacterium canetti*, and *Mycobacterium microti* can also cause tuberculosis. Symptoms of tuberculosis may include a bad cough that lasts 3 weeks or longer, weight loss, coughing up blood or mucus, weakness or fatigue, fever and chills, night sweats and/or loss of appetite.

As used herein, "lung cancer" refers to a disease of uncontrolled cell growth in tissues of the lung. This growth may lead to metastasis, invasion of adjacent tissue and infiltration beyond the lungs. The vast majority of primary lung cancers are carcinomas of the lung, derived from epithelial cells. Lung cancer is the most common cause of cancer-related death in men and the second most common in women. There are two major types of lung cancer: non-small cell lung cancer and small cell lung cancer. Non-small cell lung cancer is much more common. It usually spreads to different parts of the body more slowly than small cell lung cancer. Squamous cell carcinoma, adenocarcinoma, and large cell carcinoma are three types of non-small cell lung cancer. Small cell lung cancer also called oat cell cancer, accounts for about 20% of all lung cancer. Smoking is the number one cause of lung cancer. Another leading cause of lung cancer is on-the-job exposure to cancer-causing substances (carcinogens). Asbestos is a well-known, work-related substance that can cause lung cancer, but there are many others, including uranium, arsenic, and certain petroleum products. High levels of pollution and radiation exposure may increase the risk of lung cancer. Symptoms of lung cancer include: shortness of breath, fever without a known reason, repeated bouts of bronchitis or pneumonia, dyspnea (shortness of breath), hemoptysis (coughing up blood), chronic coughing or change in regular coughing pattern, wheezing, chest pain or pain in the abdomen, cachexia (weight loss), fatigue and loss of appetite, dysphonia (hoarse voice), clubbing of the fingernails (uncommon) and/or dysphagia (difficulty swallowing).

The therapeutic agents that may be used to address the foregoing conditions include, without limitation, antiproliferative agents, anti-inflammatory agents, antineoplastics and/or antimitotics, antiplatelet, anticoagulant, antifibrin, and antithrombin drugs, cytostatic or antiproliferative agents, antibiotics, antiallergic agents, antioxidants and other bioactive agents known to those skilled in the art.

Examples of antiproliferative agents include, without limitation, actinomycins, taxol, docetaxel, paclitaxel, rapamycin, 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, everolimus, biolimus, perfenidone and derivatives, analogs, prodrugs and co-drugs thereof.

Examples of anti-inflammatory agents include both steroidal and non-steroidal (NSAID) anti-inflammatory agents such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecrolimus and derivatives, analogs, prodrugs and co-drugs thereof.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, phe-pro-arg-chloromethylketone, dipyridamole, glycoprotein IIIb/IIIa platelet membrane receptor antagonist antibody, recombinant hirudin and thrombin, thrombin inhibitors such as Angiomax ä, calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, 4-amino-2,2,6,6-tetramethylpiperidine-1-oxyl (4-amino-TEMPO) and derivatives, analogs, prodrugs and codrugs.

Examples of cytostatic or antiproliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Examples of antiallergic agents include, without limitation, permirolast potassium.

Other compounds that may be used as therapeutic agents with method of this invention include, without limitation, alpha-interferon, genetically engineered epithelial cells, dexamethasone, antisense molecules which bind to complementary DNA to inhibit transcription, and ribozymes, antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy; antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and derivatives, analogs, prodrugs and codrugs thereof.

Other therapeutic agents include corticosteroids, paclitaxel, biolimus A9, bisphosphonates, ApoA1, mutated ApoA1, ApoA1 milano, ApoA1 mimetic peptides, ABC A1 agonists, anti-inflammatory agents, anti-proliferative agents, anti-angiogenic agents, matrix metalloproteinase inhibitors and tissue inhibitors of metalloproteinase.

The therapeutic agents of this invention are encapsulated within particles. The therapeutic agent preferably, elutes from the particle over a period from about 1 hour to about 1 year. The therapeutic agent, more preferably, elutes from the particle over a period from about 1 day to about 1 month. Presently preferred particles of this invention include, but are not limited to, hydrogel particles, polymer particles and porous silica particles.

As used herein, a "gel" or "hydrogel" refers to a water-insoluble substance that nevertheless is capable of imbibing a substantial amount of water causing the substance to swell in the process.

As used herein, a "polymer" refers to a molecule(s) composed of a plurality of repeating structural units connected by chemical bonds.

As used herein, a "polymer particle" refers to a solid or porous particle, in contrast to the shell structure of liposomes and polymersomes and the relatively open structures of hydrogel particles. Methods for adhering a bioactive agent to the surface of or integrating a bioactive agent into the structure of a polymer particle are known to those skilled in the art.

As used herein, "porous silica" refers to the oxide of silicon in porous form, expressed in $SiO_2 \cdot xH_2O$ indicating water is chemically bound in non-stoichiometric amount. Silicon dioxide is formed when silicon is exposed to oxygen or air.

Porous silica with nanometer-sized pores are generally prepared from silica powder by: a) acid deposition from $Na_2SiO_3$ solution; b) sol-gel method from organo-silicon compounds; or c) vapor deposition from a silica fume.

As used herein, "biocompatible" refers to a material, e.g., a polymer, that both in its intact, as synthesized state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

As used herein, "biodegradable", "bioerodable" or "biosoluble" refers to a material that degrades, erodes or dissolves under physiological conditions. As used herein, the terms "biodegradable", "bioerodable" or "biosoluble" are used interchangeably.

Among useful biocompatible, relatively biostable polymers are, without limitation, polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers include naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

One or more synthetic or semi-synthetic biocompatible, biodegradable polymers may also be used with this invention. As used herein, a synthetic polymer refers to one that is created wholly in the laboratory while a semi-synthetic polymer refers to a naturally-occurring polymer than has been chemically modified in the laboratory. Examples of synthetic polymers include, without limitation, polyphosphazines, polyphosphoesters, polyphosphoester urethane, polyhydroxyacids, polyhydroxyalkanoates, polyanhydrides, polyesters, polyorthoesters, polyamino acids, polyoxymethylenes, poly(ester-amides) and polyimides.

Blends and copolymers of the above polymers may also be used and are within the scope of this invention. Based on the disclosures herein, those skilled in the art will recognize those polymers and materials from which they may be fabricated that will be useful with the composition of this invention.

This invention is intended to take advantage of lung structure to deliver therapeutic agents broadly to the lungs. That is, the trachea (windpipe) through which air enters the lungs divide, just before entrance into the lungs, into two main bronchi, the right and the left. The right subdivides into three segmental bronchi while the left divides into two. These lobar bronchi divide into tertiary bronchi known as segmental bronchi. There are initially 10 segmental bronchi in each lung but during anatomical development four bronchi in the left lung fuse into two bronchi giving 8 total in that lung. The segmental bronchi divide into primary bronchioles which then divide into terminal bronchi each of which gives rise to several respiratory bronchioles that in turn divide into 2 to 11 alveolar ducts and, finally, each alveolar duct is associated with 5 or 6 alveolar sacs. It is these alveolar sacs (each being a alveolus) that are the basic anatomical unit of gas exchange in the lung and as is evident from the preceding description, there are a great many of them. In fact, there are, in a normal healthy pair of lungs, about 300 million alveoli. Each alveolus is about 0.2 mm in diameter and has a wall made of a membrane only 0.001 mm thick. If spread out flat the surface area of the alveoli would cover an area of approximately 90 $m^2$, about the size of a tennis court. The entire outer surface of the alveoli is covered with a network of capillary blood vessels originating from the pulmonary artery and eventually draining into the pulmonary vein. The capillary network is so extensive that if placed end-to-end they would stretch about 5000 km which approximates the distance from NY to London.

The capillaries of the alveoli are extremely small with an internal diameter that is smaller than that of a red blood cell, i.e., smaller than 6-8 microns. Thus, the particles of this invention will be capable of making their way through the labyrinthine network of bronchi and bronchioles and into the alveolar ducts where their progress will be stalled due to their size, preferably at present from about 10 to about 20 microns, being greater than that of the alveolar lumen they are traversing. The extremely large number of alveolar ducts results in at least two beneficial effects. Obstruction blood flow in a portion of them as the result of their being unable to progress further into the blood flow system should have very little if any observable effect on a patient. The same vast network of alveolar ducts will assure the broad dissemination of the therapeutic agent-containing particles throughout the lungs which will result in intimate contact with whatever causal factor is responsible for the disease itself or symptoms thereof in the vicinity of the alveolar sacs, which as discussed previously are generally the end targets of most lung diseases.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed:

1. A method for treating lung disease in a patient in need thereof, comprising:
    providing a plurality of particles that have a smallest cross-sectional dimension of 10 microns sufficient to obstruct alveolar capillaries, wherein the plurality of the particles are selected from the group consisting of hydrogel particles, polymer particles and porous silica particles;
    encapsulating within, adhering to, or incorporating into the structure of, the particles a therapeutic agent; and
    administering the particles directly into the right ventricle or right atrium of the heart or into the proximal portion of the venous system feeding the right atrium of the heart or the pulmonary artery in an amount such that the portion of obstructed alveolar capillaries has no observable effect on said patient.

2. The method of claim 1, wherein administering the particles comprises intravenous delivery.

3. The method of claim 1, wherein administering the particles comprises direct injection into the right ventricle or right atrium of the heart.

4. The method of claim 1, wherein administering the particles comprises using a catheter.

5. The method of claim 1, wherein the particles are biodegradable.

6. The method of claim 1, wherein the therapeutic agent elutes from the particle over a period from about 1 hour to about 1 year.

7. The method of claim 1, wherein the therapeutic agent elutes from the particle over a period from about 1 day to about 1 month.

8. The method of claim 1, wherein the lung disease is selected from the group consisting of asthma, chronic obstructive pulmonary disease (COPD), chronic bronchitis, emphysema, pulmonary hypertension, pulmonary fibrosis, sarcoidosis, influenza, pneumonia, tuberculosis and lung cancer.

* * * * *